(12) United States Patent
Hein et al.

(10) Patent No.: US 8,636,675 B2
(45) Date of Patent: Jan. 28, 2014

(54) METHOD AND DEVICE FOR THE EXTRACTION OF A BODY FLUID

(75) Inventors: Heinz-Michael Hein, Udligenswil (CH); Reto Abt, Bünzen (CH); Stephan Korner, Cham (CH); Irio Giuseppe Calasso, Arth (CH); Emad Sarofim, Hagendorn (CH); Patrick Griss, Otelfingen (CH); Rainer Jaeggi, Thalwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 185 days.

(21) Appl. No.: 12/901,290

(22) Filed: Oct. 8, 2010

(65) Prior Publication Data

US 2011/0028862 A1 Feb. 3, 2011

Related U.S. Application Data

(60) Division of application No. 11/868,505, filed on Oct. 7, 2007, now Pat. No. 7,833,172, which is a continuation of application No. PCT/EP2006/003141, filed on Apr. 6, 2006.

(30) Foreign Application Priority Data

Apr. 7, 2005 (EP) .................................. 05007580

(51) Int. Cl.
| | | |
|---|---|---|
| A61B 5/00 | (2006.01) | |
| A61B 17/14 | (2006.01) | |
| A61B 17/32 | (2006.01) | |
| B65D 81/00 | (2006.01) | |

(52) U.S. Cl.
USPC ............ 600/583; 600/584; 606/181; 606/182

(58) Field of Classification Search
USPC .......................... 600/583, 584; 606/181, 182
See application file for complete search history.

(56) References Cited

U.S. PATENT DOCUMENTS

| | | | |
|---|---|---|---|
| 5,069,223 A | 12/1991 | McRae | |
| 5,857,983 A | 1/1999 | Douglas et al. | |
| 5,951,492 A | 9/1999 | Douglas et al. | |
| 6,706,159 B2 * | 3/2004 | Moerman et al. | 204/403.03 |
| 7,025,774 B2 | 4/2006 | Freeman et al. | |

(Continued)

FOREIGN PATENT DOCUMENTS

| | | |
|---|---|---|
| EP | 1 169 974 | 1/2002 |
| EP | 1 238 632 | 11/2002 |

(Continued)

*Primary Examiner* — Rene Towa
*Assistant Examiner* — Adam Eiseman
(74) *Attorney, Agent, or Firm* — Bose McKinney & Evans LLP

(57) ABSTRACT

The present invention provides a method and a device for piercing a body part and determining whether a sufficient volume of blood has been withdrawn. A lancing element is rapidly inserted into a body part in a forward phase and retracted quickly to a lesser puncturing depth. Subsequently, the lancing element is retracted slower than during the first retraction movement and the distance retracted during the second retraction is shorter than the first retraction movement. During the second retraction movement, body fluid is collected in a collection phase by a capillary structure of the lancing element. Contact between the lancing element and the body fluid is detected after the forward phase at the beginning and the end of a waiting period.

25 Claims, 5 Drawing Sheets

(56) References Cited

U.S. PATENT DOCUMENTS

| | | |
|---|---|---|
| 2002/0042594 A1* | 4/2002 | Lum et al. .................... 604/117 |
| 2002/0065481 A1 | 5/2002 | Cory et al. |
| 2002/0168290 A1 | 11/2002 | Yuzhakov et al. |
| 2003/0018282 A1 | 1/2003 | Effensauser et al. |
| 2003/0083641 A1 | 5/2003 | Angel et al. |
| 2003/0083645 A1 | 5/2003 | Angel et al. |
| 2003/0083685 A1 | 5/2003 | Freeman et al. |
| 2003/0199911 A1 | 10/2003 | Boecker et al. |
| 2003/0212346 A1 | 11/2003 | Yuzhakov et al. |
| 2003/0216661 A1 | 11/2003 | Davies |
| 2004/0127818 A1 | 7/2004 | Roe et al. |
| 2004/0260325 A1 | 12/2004 | Kuhr et al. |
| 2005/0085839 A1 | 4/2005 | Allen et al. |
| 2006/0100542 A9* | 5/2006 | Wong et al. .................... 600/583 |
| 2006/0178573 A1* | 8/2006 | Kermani et al. ............... 600/347 |
| 2007/0232956 A1* | 10/2007 | Harman et al. ................ 600/573 |
| 2008/0082023 A1 | 4/2008 | Deck et al. |
| 2008/0208079 A1* | 8/2008 | Hein et al. .................... 600/583 |
| 2010/0145229 A1* | 6/2010 | Perez et al. .................... 600/583 |

FOREIGN PATENT DOCUMENTS

| | | |
|---|---|---|
| WO | WO 97/42883 | 11/1997 |
| WO | WO 02/100251 | 12/2002 |
| WO | WO 03/009759 | 2/2003 |
| WO | WO 2004/080306 | 9/2004 |
| WO | WO 2004/091693 | 10/2004 |

\* cited by examiner

METHOD AND DEVICE FOR THE EXTRACTION OF A BODY FLUID

RELATED APPLICATIONS

This application is a divisional of application Ser. No. 11/868,505, filed Oct. 7, 2007 now U.S. Pat. No. 7,833,172, which is a continuation application of International Application PCT/EP2006/003141, filed Apr. 6, 2006, which claims priority to EP 05007580.3, filed Apr. 7, 2005, which are hereby incorporated by reference in their entirety.

BACKGROUND

The present invention relates to methods and devices for withdrawing body fluid in which a lancing element is inserted into the skin of a body part and body fluid is collected by a capillary structure of the lancing element.

Methods and devices are known for withdrawing small amounts of body fluid and are used by diabetics to self-monitor their blood sugar several times daily. These corresponding methods and devices are directed toward a disposable measuring microneedle disposed in a hand-held device to generate a skin puncture, to remove a small amount of blood using capillary forces, and to analyze the blood sample. With this type of integrated system, a layperson can simply and rapidly carry out the necessary steps during a substantially automated measuring process. In order to achieve this, however, it is important that the lancing and collecting processes are adapted to the disposable microneedle such that blood or other body fluid can be collected efficiently, rapidly and without causing significant pain to the user.

To meet these goals, known devices may detect when the skin is contacted in order to achieve a defined lancing depth for the control of the forward-directed lancing movement. However, such movement control has to be adapted to the desired lancing speed using a very complex apparatus. Additionally, such a system cannot be used to provide information about the actual success of the blood collection.

In order to optimize the collection of blood samples, document WO 03/009759 describes a method in which a puncture is made and the lancing unit, having a capillary structure, is then retracted along a portion of the lancing path and is left there for a few seconds to collect the sample. This opens a portion of the lancing channel such that body fluid can collect therein and subsequently enter the capillary structure.

A lancing system described in document WO 2004/080306 detects a characteristic parameter (e.g., impedance) during the lancing movement and optionally during the retraction. This detection only serves as a skin detection in order to indicate the penetration depth, penetration stability, or residence time (i.e., duration of penetration and retraction) for the user.

SUMMARY OF THE INVENTION

The present invention addresses the disadvantages of the prior art and provides a device and method for optimized collection of body fluid, particularly with respect to reliability, efficiency, pain minimization and hygiene.

The teachings herein are based on providing an immediate determination of whether the liquid collection is successful instead of conducting a lancing check during a subsequent phase of the blood collection. Accordingly, contact between the lancing element and the body fluid is detected after the forward movement and during a collection phase while the lancing element is inside the body part. Therefore, a detection means or element is provided for a device to detect contact between the lancing element and the body fluid after the forward movement and during the collection phase. In this manner it is possible to optimize withdrawal of body fluid, because when liquid contact has been detected, it means that body fluid must have flowed from the puncture wound to or past the detection means or element. This process is also appropriate for situations which also consider user-specific parameters such as the local skin condition and blood circulation. The reliability in obtaining the minimum amount of blood needed for a successful test is increased and withdrawal of blood with minimal pain becomes possible because the duration of blood withdrawal can be adapted as a function of liquid contact.

Another embodiment uses an improved flow of blood from the puncture wound through a reduced-pain zone rather than carrying out the collection process at the puncture wound. Accordingly, a method is provided in which after the forward movement, the lancing element is retracted by a first distance during a retraction phase and by a second distance during a subsequent collection phase. The retraction phase is shorter in duration than the collection phase and the first distance is larger than the second distance, and the second distance is greater than zero. An exemplary embodiment provides a device that includes a lancing drive designed to retract the lancing element by a first distance during the retraction phase and by a second distance during the collection phase, wherein the retraction phase has a shorter duration than the collection phase and the first distance is larger than the second distance. A lancing channel is thereby created in a blood zone of the skin in a rapid and pain-reduced manner while the collection process continues for a period of time required to self-transport the liquid or blood in the capillary structure in a less sensitive outer skin layer.

Surprisingly, it has been found that slow retraction of the lancing element results in a considerably improved collecting efficiency than when the lancing element is not retracted (i.e., a static collection position). Without wishing to be tied to any specific theory, one possible explanation for this is that after the rapid lancing movement, the skin is pushed in by the lancing member or tip and this pressing force initially prevents the flow of blood. However, the skin relaxes during the slow retraction of the collection phase so that blood can flow in an improved manner. It is also conceivable that a suction effect is achieved by the retraction of the lancing element so that additional blood is available or withdrawn. In this regard, collecting body fluid in the lanced state (i.e., while the tip of the lancing element is still beneath the skin surface) is hygienically favorable and efficient for the metered withdrawal of small amounts of liquid or body fluid.

The lancing member or tip rapidly exits the pain region of the body part or skin rapidly as a result of the rapid retracting movement into a retraction position having a smaller puncture depth. After a waiting period, it is then determined whether additional blood flows via the lancing channel formed in the skin to this outer, non-blood-delivering layer of skin. When there is liquid contact, it can be assumed that there is a high collection success rate. In addition, liquid can be hygienically collected while the lancing member or tip is still in the skin without a significant amount of blood escaping. A measurement of the impedance with the incorporation of the lancing member as an electrode is especially advantageous for detecting the liquid contact. It can be determined whether body fluid has been received from the body part or from the puncture wound when contact has been detected with the body fluid. The probability that body fluid has been successfully collected is increased considerably by verifying contact.

This also allows one to continue the collection process for the optimal collection period. Optionally, an error signal is generated in the absence of contact and the collection process is thereby discontinued.

After the rapid retraction of the lancing element, the body fluid is collected during the collection phase in the outer, substantially pain-free skin layer. In this process, the lancing element is steadily retracted or retracted at a variable speed at least during a portion of the collection phase, which considerably improves the collecting efficiency. The collection time should be sufficient to provide an adequate collection of liquid by capillary action.

In particular, all disclosed embodiments can be combined with one another with regard to the detection of body fluid and the lancing profiles.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
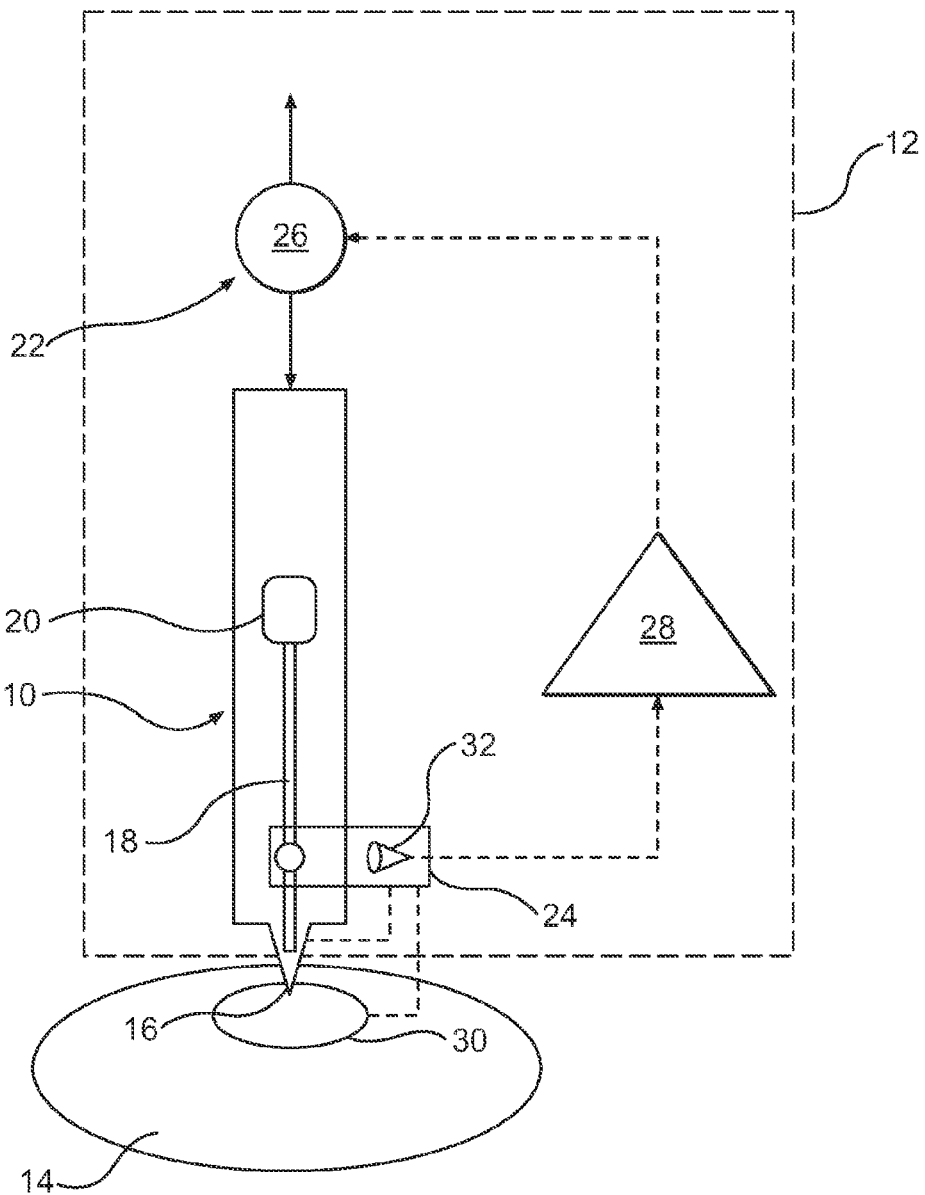
FIG. 1 is a schematic diagram of a device for withdrawing and analyzing body fluid from a body part.
Figures 2, 3:
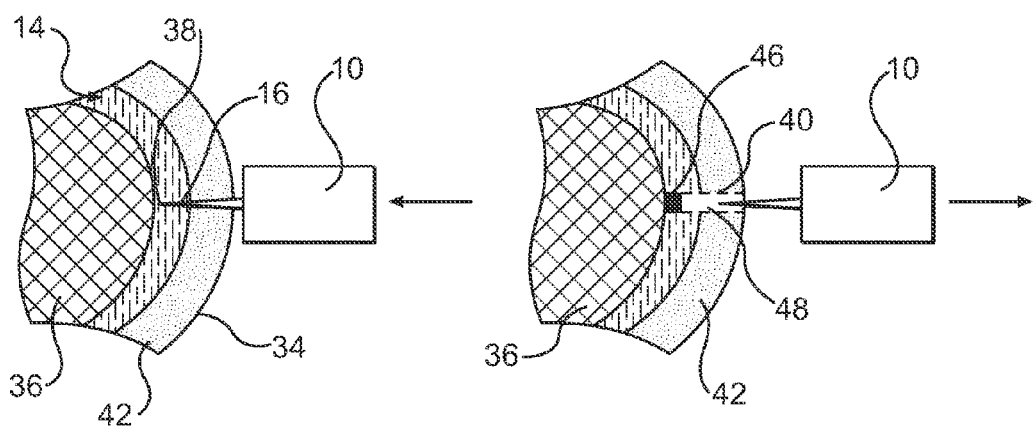
FIGS. 2-5 are fragmentary sectional views of a lancing device shown in various lancing positions.

The device shown in FIG. 1 is used for self-withdrawal of a blood sample by a user for analytical purposes. The device comprises a lancing element 10 as a disposable article for fluid collection and a hand-held device 12 for automatically handling the lancing element 10.

The lancing element 10 is designed as a so-called "microsampler" for collecting a small amount of fluid from a body part 14 such as, for example, a fingertip. The lancing element 10 is a flat-shaped member made of a thin, high-grade steel sheet and has a distal-shaped tip 16 as a lancing member which is connected via a semi-open, groove-shaped capillary channel 18 to a collection site 20. The collection site 20 can be designed as a reaction area for detecting an analyte, e.g., glucose. The detection of blood glucose, in particular, by means of contact-free optical methods, is known in the art. Optionally, the collected blood can also be transported into an analytical unit in order to perform testing ex situ.

The hand-held device or instrument 12 has a lancing drive 22 for controlling the forward and backward movement of the lancing element 10 and it has a detection mechanism 24 for detecting contact between the lancing element 10 and blood during a collection phase. Lancing drive 22 comprises a mechanical and/or electrical drive unit 26 which is coupled to the lancing element 10. In particular, a two-step hybrid drive can be provided in which a rapid movement is undertaken by a mechanism, for example, a drive spring or drive guide block, whereas a slower controlled movement is carried out by an electric motor. Alternatively, the lancing stroke can also be driven by an electromagnetic drive. Lancing drive 22 additionally comprises a control unit 28 to control or regulate the process of blood withdrawal and, in particular, the lancing movement. It is desirable to use a microcontroller for this purpose, which permits the adaptation of the method or device parameters for a specific user.

The detection mechanism 24 can detect contact with blood during the collection phase by a measurement of impedance between the lancing member or tip 16 and a pressure ring 30 as a counter-electrode. In this embodiment, the pressure ring 30 is axially penetrated by the lancing member or tip 16 and is in contact with the body part 14. A lancing member or tip 16 consisting of electrically conductive material can be safely actuated by an alternating voltage signal, e.g., 4 Vpp (peak power point) and 10 kHz, in which the impedance in the electrical path between the lancing member or tip 16 and the counter-electrode is significantly decreased by fluid contact. The control device 32 enables the success of blood collection to be verified by detecting liquid contact.

FIGS. 2-5 illustrate a blood collection process by the lancing element 10. First, the lancing member or tip 16 is inserted in a puncturing direction into a skin surface 34 of a body part 14 to a predetermined depth, such that a fluid-delivering zone or layer 36 in the dermis is reached. For blood collection, the blood capillaries can be opened by the lancing member end or tip 16 in this region. At the same time, the pain sensation in this deeper region 36 is higher due to the nerve cells that are present there. For this reason, it is advantageous to retract the lancing element 10 from a deepest puncture position 38 or puncture depth (FIG. 2) to a retraction position 40 (FIG. 3) of lesser lancing depth immediately after the forward movement. This retraction or lesser depth position 40 is advantageously located in the region of the epidermis 42 and, in particular, in the stratum corneum 44 (see FIG. 10). A certain amount of time transpires after the rapid retraction of lancing element 10 before fluid 46 flows into the epidermis through the puncture channel 48 that has been generated.

Figure 10:
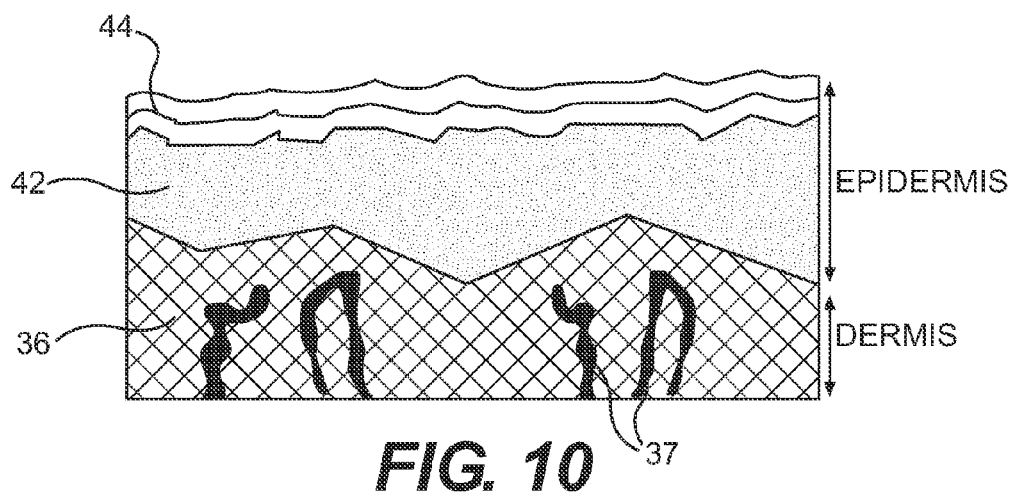
FIG. 10 is a cross-sectional view of human skin.

The dimensions of the layer structure of human skin are schematically illustrated in FIG. 10. The epidermis 42, with the stratum corneum 44 as the outermost skin layer, has a depth of about 0.5 to 1 mm, whereas the dermis 36 containing blood capillaries 37 extends to a depth of a few millimeters.

Referring again to FIG. 4, fluid contact is detected in the retracted or lesser depth collecting position 40 by the detection mechanism 24, and the detection is used to determine whether the collection was successful. Fluid contact is determined after a waiting period following the forward puncturing movement, which allows the collection time to be optimized. If contact with the liquid is verified, it can be safely assumed that liquid has subsequently flowed from the puncture wound towards the lancing member or tip 16. If, in contrast, no fluid contact has been verified after the waiting period, the measurement can be discontinued by the control device 32. Therefore, false results due to the absence of blood or an amount of blood that is too small to detect can be avoided. The control device 32 may provide the user with a corresponding signal and result.

Figures 4, 5:
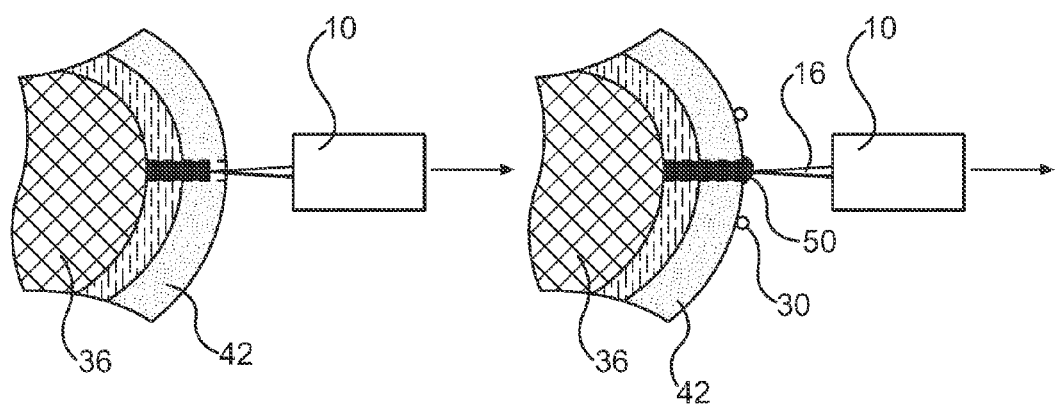

The collection process does not have to be carried out statically (i.e., the lancing element remaining stationary), but rather can be carried out during an additional retracting movement of the lancing element 10. Additionally, liquid collection on the skin surface 34 is also possible as shown in FIG. 5. In this case, contact with the liquid can be reliably detected by the lancing member or tip 16 as a measuring electrode which dips or penetrates into a drop of fluid 50 on the skin surface 34 and is thus in fluid contact with the skin, and by the pressure ring 30 resting against the skin and acting as a counter-electrode. The pressure ring 30 is additionally intended to support the blood flow under pressure and to open the wound so that contact is made between the lancing member and the skin and thus the pain for the user is minimal.

The lancing profiles shown in FIGS. 6 to 9 are particularly advantageous for collecting blood in a manner that is successful and as pain-free as possible. In this embodiment, the term lancing profile is to be understood as the lancing movement profile plotted as a function of lancing depth versus time.

Figure 6:
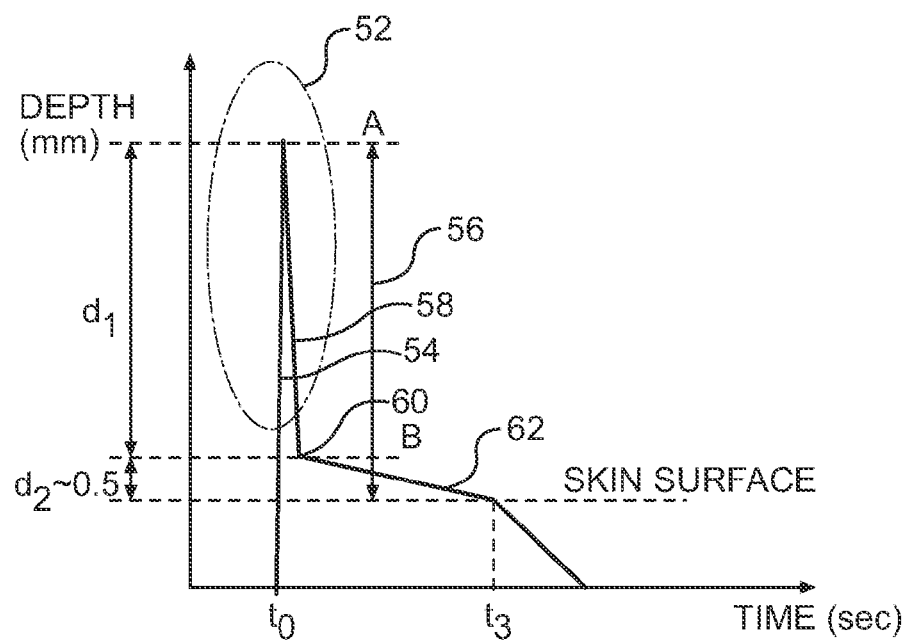
FIGS. 6-9 are graphical representations of various lancing profiles when using the lancing element.

In the lancing profile shown in FIG. 6, the lancing member is rapidly inserted in a forward, puncturing movement 54 to a predetermined puncture depth 56 into the blood-delivering, pain-sensitive skin region 52 and immediately retracted in a retraction movement 58 to a lesser depth of about 0.5 mm. The retraction phase is of the same order of magnitude as the duration of the forward movement, viz., a few hundred microseconds. The retraction position of lesser depth 60 can be positioned in the region of the stratum corneum and thus outside of the pain region 52. A collection phase 62 subsequently occurs in which blood is collected while the lancing element is slowly further retracted until the tip reaches the skin surface. This collection phase 62 lasts a few seconds, whereby the distance $d_2$ traveled by the lancing member is substantially smaller than the retraction distance $d_1$ during the retraction phase 58. It is believed that as a result of the subsequent slower retraction, the skin relaxes so that the lancing channel does not immediately become blocked again.

Since the collection process requires a certain amount of time, it is desirably carried out in the essentially nerve-free outer skin zone. The collection process advantageously takes place while the lancing element is still inserted in the skin and is also avoids fluid discharge onto the skin and thus enables a particularly hygienic withdrawal process. Furthermore, fluid which has already discharged onto the skin surface can only be cleanly removed or collected with the lancing element 10 (FIG. 1) when the capillary force of the capillary channel 18 is large enough at this position. This is the case when the lancing member or tip 16 is at least slightly inserted into the skin because the capillary depth becomes smaller towards the tip and thus the capillary force also decreases.

Electrical or electromagnetic drives are more advantageous than purely mechanical drives for achieving the lancing profile depicted in FIG. 6, because in the latter case bouncing and vibratory effects are more difficult to control. Instead, dampening can be more simply achieved by electrical rather than mechanical means.

To adjust the lancing depth in a defined manner, the skin surface can, for example, be detected by an impedance measurement before the actual lancing process. In this case, the position of the skin surface can be detected during a slow forward movement of lancing element 10.

Switching between the various regions of the lancing profile can either be controlled by position (depth) or time. The transition between the regions with different speeds can occur by a discontinuous change or it can be a smooth transition by, e.g., a continuous change in speed. The continuous movement has the advantage that less energy is required to drive the lancing element and the control of the lancing movement is simplified.

Figure 7:
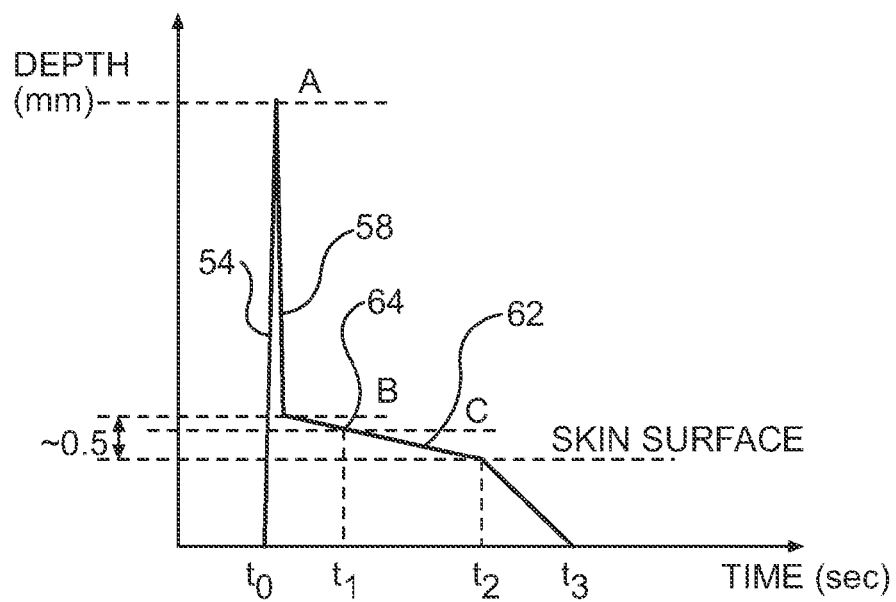

The lancing profile shown in FIG. 7 differs only by an additional step 64 during the collection phase 62. In this embodiment, after the rapid retraction to depth B, there is a slightly slower retraction to depth C and the skin relaxes during this interval. The actual collection process then occurs at an even slower retraction speed from depth C to the skin surface. This shortens the entire lancing and collecting process.

Figure 8:
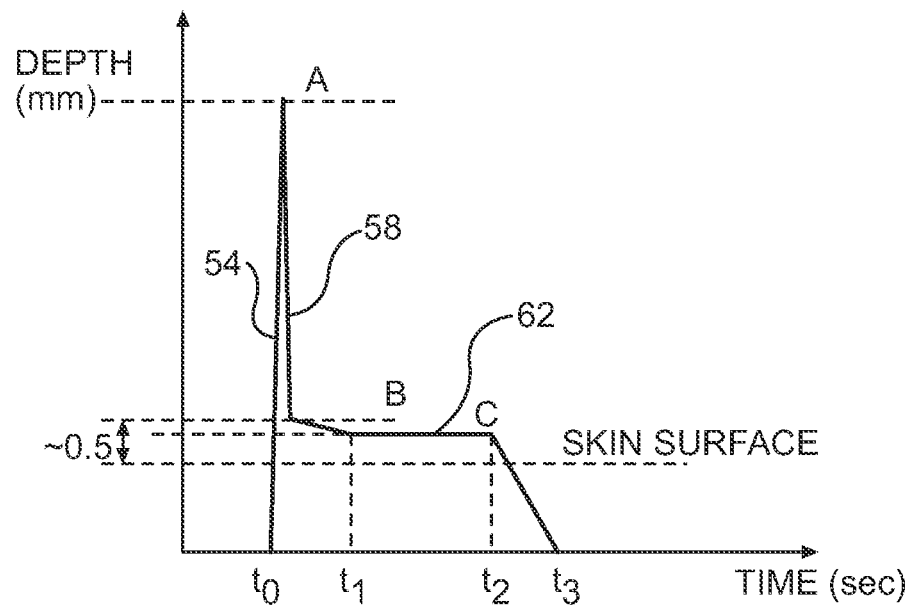

A similar embodiment of a lancing profile is shown in FIG. 8 in which, after the rapid retraction phase 58, skin relaxation is achieved by a slow retraction of the lancing member until time $t_1$, and subsequently collection is continued until time $t_2$ while the lancing member is at rest. In this embodiment, lateral movement of the lancing member relative to the skin can be felt by the user.

Figure 9:
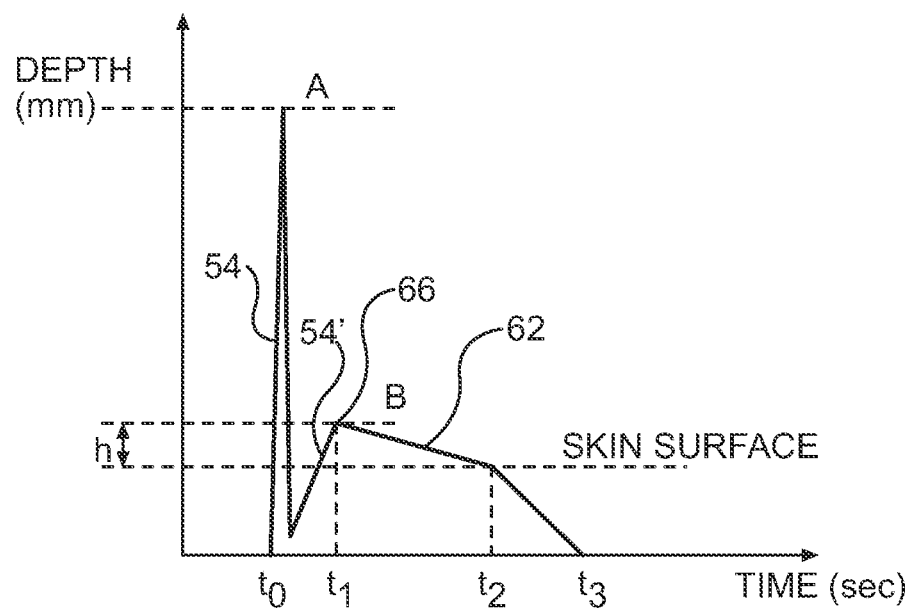

In the lancing profile shown in FIG. 9, the lancing member is completely retracted from the skin after a first rapid forward movement 54 and the skin is subsequently lanced again to a lesser lancing depth in a second forward movement 54'. At this position, blood contact is then detected and the collection process 62 is subsequently carried out while slowly retracting the lancing member until it reaches the skin surface. The advantage of this lancing profile is that any bouncing or instability of the lancing member takes place outside of the skin and thus no dampening is required, which greatly reduces the demands on the actuators.

This lancing profile lends itself to a simple control variant. Initially, the skin surface can be detected before time $t_0$ in order to accurately determine the lancing depth. This process could be carried out by an inductance or impedance measurement by slowly moving the lancing element towards the skin until its surface is contacted as described above. The first lancing process (rapidly in and rapidly out) can then immediately take place in an uncontrolled manner, i.e., without feedback from a control circuit. This has the advantage, especially when an electromagnetic coil drive is used, of eliminating the use of rapid and expensive control electronics. In the case of a hybrid drive, this rapid lancing process would be performed by the mechanical part (e.g., a spring drive or guide block drive). After the first lancing action, the lancing member is moved forward more slowly than previously (phase 54'). This movement can also take place without a control loop. Once the skin surface is reached, which can optionally be detected by renewed skin detection, a control signal can be triggered which triggers the remaining portion of the lancing profile (i.e., the collection phase). A reversal point 66 can be established relative to the trigger signal conducting the forward movement for a predetermined time. This predetermined time must be sufficiently short to avoid re-penetrating the pain zone 52. The collection process from $t_1$ until $t_2$ can then take place via simple control and without regulating position. Afterwards, the lancing element is retracted into the device until time $t_3$, at which time the lancing member is removed from the skin.

Figure 11A:
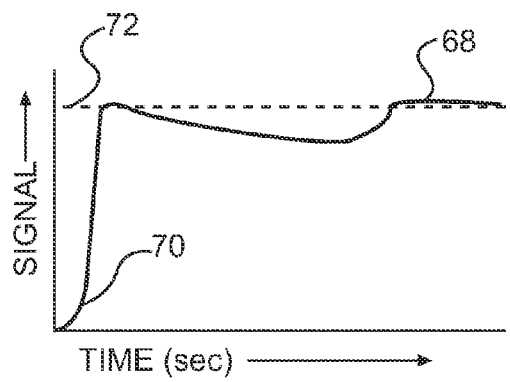
FIGS. 11a-11c are graphical representations of a measured signal as a function of time at various stages of a lancing process.
Figure 11B:
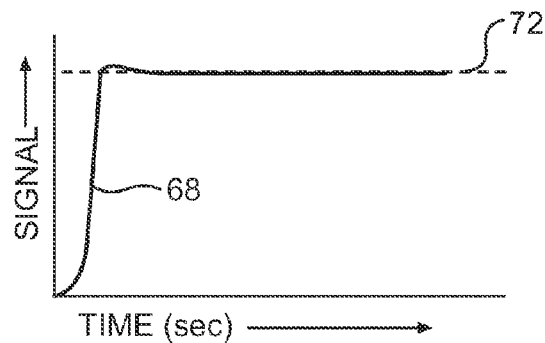
Figure 11C:
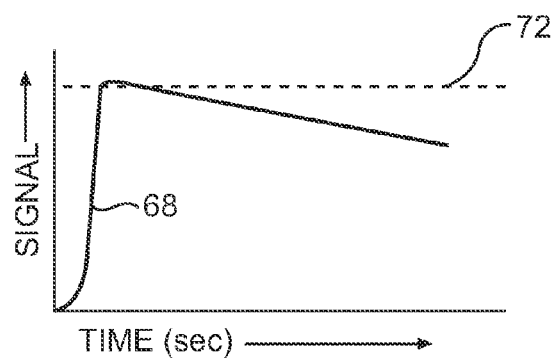

The profile of a measurement signal 68 over time is shown in more detail in FIGS. 11a-11c. When dry skin is penetrated, the conductivity initially increases more slowly up to a bending point 70, until the tip 16 (FIG. 2) contacts blood in the dermis layer 36, which causes a rapid increase in the signal. The signal level 72 is reached at the end of the forward movement, which is characteristic for direct liquid contact and can thus serve as a reference signal. In this regard, it should be noted that when skin contact is made, it is initially the conductivity or impedance of the skin area between the tip 16 and the ring electrode 30 (FIG. 5), and the ring radius is thus relevant. When the tip 16 contacts the body fluid 50, the effective electrode area increases abruptly and the signal is only influenced by the thickness of the skin layer between the blood zone 36 and the ring 30 resting thereon, which is substantially less than the ring radius. Hence, especially when measuring capacitance, it is advantageous when the ring 30 is electrically insulated from the skin surface 44 (FIG. 10).

Thus, according to FIG. 11a, at the end of the forward movement at which the fluid-delivering zone 36 is reached (FIG. 2), the signal level 72 is attained and this is characteristic (and can optionally be determined empirically) of liquid contact. During the subsequent retraction into the collecting position 40 (FIG. 3), a short time may elapse before the body fluid reaches the retracted needle tip 16. Accordingly, the signal decreases during retraction and again reaches the maximum value or reference level 72 when the tip 16 contacts the blood a second time. Thus, after waiting a predetermined amount of time, it is possible to determine the success of the blood collection by determining whether the signal level 72 is reached again.

If there is rapid flow of body fluid from the puncture wound, the contact between the liquid and the retracted tip 16 is not disrupted and the measurement signal 68 remains constant, as shown in FIG. 11b. A positive verification of success is possible in this situation as well.

In contrast, FIG. 11c illustrates a profile in which there is little or no flow of blood from the puncture wound, and the measurement signal 68 further decreases even in the retracted position. A fault is detected after a defined waiting period elapses on the basis of the change of the measurement signal 68. In this case, a collection of body fluid has probably not been successful. A critical change in the signal 68 can be determined by a comparison with the signal level 72 measured at the start of the waiting period or by evaluating the slope of the measurement signal 68 over time. As a result, the measurement can then be terminated and the user can be warned.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of collecting body fluid with a lancing element having a tip and a capillary structure formed in the lancing element, comprising:
    inserting the tip of the lancing element into the skin of a body part to a puncture depth;
    retracting the tip from the puncture depth to a lesser depth than the puncture depth;
    retracting the tip from the lesser depth toward the skin surface, wherein the retracting of the tip from the puncture depth to the lesser depth is faster than the retracting of the tip from the lesser depth toward the skin surface;
    detecting contact between the lancing element and the body fluid after the tip has been retracted to the lesser depth;
    collecting body fluid with the lancing element; and
    determining from the detecting step whether a sufficient volume of body fluid has been collected by the lancing element.

2. The method of claim 1, further comprising:
    detecting contact between the lancing element and the body fluid when the tip is located at about the puncture depth; and
    the determining step comprising comparing a first signal generated from the detecting of contact when the tip is located at about the puncture depth to a second signal generated from the detecting of contact after the tip has been retracted to the lesser depth.

3. The method of claim 2, wherein a sufficient volume of body fluid is determined to have been collected by the lancing element when the first signal and the second signal are substantially the same.

4. The method of claim 3, further comprising triggering an error state when the first signal and the second signal are substantially different.

5. The method of claim 1, further comprising:
    forming a lancing channel in the skin during the retraction of the tip from the puncture depth to the lesser depth;
    at least partially evacuating the lancing channel during the retraction of the tip from the puncture depth to the lesser depth;
    waiting an amount of time after the retracting of the tip to the lesser depth to allow the body fluid to enter the lancing channel; and
    then performing the step of detecting contact between the lancing element and the body fluid.

6. The method of claim 1, further comprising applying a contact element against the skin, wherein the lancing element comprises electrically conductive material and the contact between the lancing element and the body fluid is detected by monitoring an electrical parameter between the contact element and the lancing element.

7. The method of claim 6, wherein the detecting step comprises measuring an electrical parameter.

8. The method of claim 7, wherein the electrical parameter comprises impedance.

9. The method of claim 7, further comprising detecting contact between the lancing element and the body fluid during the step of retracting the tip from the puncture depth to the lesser depth, wherein the electrical parameter reaches a reference value when the tip is located at about the puncture depth, then deviates from the reference value after the tip is retracted from the puncturing depth, and then substantially returns to the reference value after the tip reaches the lesser depth.

10. The method of claim 1, wherein the detecting contact comprises an optical measurement.

11. The method of claim 1, wherein the lesser depth is located in the region of the stratum corneum.

12. The method of claim 1, further comprising:
    removing the tip of the lancing element from the skin after the tip is retracted to the lesser depth;
    reinserting the tip into the skin; and
    wherein, the detecting contact between the lancing element and the body fluid after the tip reaches the lesser depth is performed after the reinsertion.

13. The method of claim 1, wherein the body fluid is collected via the capillary structure, the capillary structure being vacated when the tip moves from the puncture depth to the lesser depth.

14. A lancing device for collecting body fluid, comprising:
    a housing;
    a lancing element reciprocably mounted in the housing, the lancing element including a tip that is exposed for puncturing a body part and the lancing element including a capillary structure adapted to collect body fluid;
    a lancing drive connected to the lancing element, the lancing drive configured to move the lancing element in a forward phase to a puncture depth, a retraction from the puncture depth to a lesser depth, and a retraction from the lesser depth toward the skin surface, the retraction from the puncture depth to the lesser depth being faster than the retraction from the lesser depth toward the skin surface; and a detection mechanism adapted to detect contact between the lancing element and the body fluid by measuring a signal that varies as a function of contact between the lancing element and the body fluid, the detection mechanism configured to measure and compare the signal at the beginning and at the end of a waiting period that is initiated after the forward phase.

15. The lancing device of claim 14, wherein the detection mechanism is configured to determine from the comparison whether a sufficient volume of body fluid has been collected.

16. The lancing device of claim 14, wherein the detection mechanism initiates an error signal if it is determined that a sufficient volume of body fluid has not been collected.

17. The lancing device of claim 14, wherein the detection mechanism comprises an electrically insulated contact element configured for contact with the body part.

18. The lancing device of claim 17, wherein the contact element comprises a ring.

19. The lancing device of claim 17, wherein the lancing element comprises a first electrode and the contact element comprises a second electrode.

20. The lancing device of claim 19, wherein the detection mechanism measures impedance.

21. The lancing device of claim 14, wherein the detection mechanism measures an optical parameter.

22. A method of collecting body fluid with a lancing element having a tip and a capillary structure formed in the lancing element, comprising:

inserting the tip of the lancing element into the skin of a body part to a puncture depth;

retracting the tip from the puncture depth to a lesser depth than the puncture depth;

removing the tip of the lancing element from the skin after the tip is retracted to the lesser depth;

reinserting the tip into the skin;

then detecting contact between the lancing element and the body fluid after the tip has been retracted to the lesser depth; and determining from the detecting step whether a sufficient volume of body fluid has been collected by the lancing element.

23. The method of claim 1, further comprising maintaining the tip stationary for a period of time after the tip reaches the lesser depth.

24. The method of claim 23, further comprising collecting body fluid while the tip is maintained stationary.

25. The method of claim 1, further comprising collecting body fluid during the step of retracting the tip from the lesser depth toward the skin surface.

* * * * *